United States Patent [19]

Wolfbeis et al.

[11] Patent Number: 5,407,829
[45] Date of Patent: Apr. 18, 1995

[54] METHOD FOR QUALITY CONTROL OF PACKAGED ORGANIC SUBSTANCES AND PACKAGING MATERIAL FOR USE WITH THIS METHOD

[75] Inventors: Otto S. Wolfbeis; Helmut List, both of Graz, Austria

[73] Assignee: AVL Medical Instruments AG, Schaffhausen, Switzerland

[21] Appl. No.: 83,330

[22] Filed: Jun. 29, 1993

Related U.S. Application Data

[63] Continuation-in-part of Ser. No. 674,940, Mar. 26, 1991, abandoned.

[30] Foreign Application Priority Data

Mar. 27, 1990 [AT] Austria ................... 713/90

[51] Int. Cl.⁶ ............................................. G01N 31/00
[52] U.S. Cl. ............................................ 436/1; 422/56; 422/57; 422/58; 422/87; 422/91; 422/82.07; 422/82.08; 426/87; 435/291; 436/2
[58] Field of Search ................ 436/1, 2; 422/56-58, 422/87, 91, 82.07, 82.08; 426/87, 88, 232, 383; 435/291; 250/458.1, 459.1; 356/402, 417, 317, 318; 116/206, 207, 216, DIG. 41; 206/459.1

[56] References Cited

U.S. PATENT DOCUMENTS

| | | | |
|---|---|---|---|
| 2,762,711 | 9/1956 | Zopf | 426/88 |
| 3,067,015 | 12/1962 | Lawdermilt | 426/87 |
| 3,198,163 | 8/1965 | Williams | 116/206 |
| 3,904,373 | 9/1975 | Harper | 422/57 |
| 4,003,709 | 1/1977 | Eaton et al. | 426/87 |
| 4,019,865 | 4/1977 | Sinclair et al. | 422/86 |
| 4,328,181 | 5/1982 | Anders et al. | 422/56 |
| 4,557,900 | 12/1985 | Heitzman | 422/56 |
| 4,746,616 | 5/1988 | Honigs et al. | 436/20 |
| 4,857,472 | 8/1989 | Wolfbeis | 422/91 |
| 4,910,406 | 3/1990 | Craig et al. | 436/1 |
| 4,945,060 | 7/1990 | Turner et al. | 435/291 |
| 5,053,339 | 10/1991 | Patel | 436/2 |
| 5,066,475 | 11/1991 | Yoshinaka et al. | 423/622 |
| 5,081,012 | 1/1992 | Flanagan et al. | 435/291 |
| 5,095,283 | 3/1992 | Patel | 422/56 |
| 5,096,813 | 3/1992 | Krumhar et al. | 436/1 |
| 5,108,932 | 4/1992 | Wolfbeis | 250/458.1 |
| 5,114,676 | 5/1992 | Leiner et al. | 422/82.07 |

FOREIGN PATENT DOCUMENTS

| 105870 | 2/1987 | European Pat. Off. | |
| 2742756 | 4/1979 | Germany | 436/2 |

*Primary Examiner*—W. Gary Jones
*Assistant Examiner*—Laura E. Edwards
*Attorney, Agent, or Firm*—Watson, Cole, Grindle & Watson

[57] ABSTRACT

For quality control of packaged organic substances, preferably packaged foods and drugs, the materials to be examined are brought into contact with a planar optical sensor element which is applied on the inside of the wrapping and responds to a change in the gas composition in the gas space above the sample by a change in color or fluorescence. The change of one of the optical properties of the sensor element is detected visually or opto-electronically.

15 Claims, 1 Drawing Sheet

METHOD FOR QUALITY CONTROL OF PACKAGED ORGANIC SUBSTANCES AND PACKAGING MATERIAL FOR USE WITH THIS METHOD

CROSS REFERENCE TO RELATED APPLICATION

This application is a continuation-in-part of application Ser. No. 674,940, filed Mar. 26, 1991, now abandoned.

BACKGROUND OF THE INVENTION

The invention relates to a method for the quality control of packaged organic substances, preferably packaged foods, luxury foods and drugs, and to an advantageous packaging material for use with this method.

Whereas in unpackaged foods and beverages bacterial decomposition is detected easily by its smell or by means of sampling, detection is not so easy in packaged foodstuffs, since the gaseous products of bacterial decomposition, which are causing the smell, cannot penetrate tile wrapping. The main odorous substances involved in this process of decay are hydrogen sulphide, ammonia, organic sulphides (mercaptans) and organic amines (e.g. putrescine, cadaverine). At the same time, the activity of aerobic bacteria will cause a decrease in oxygen partial pressure and an increase in $CO_2$ partial pressure.

DESCRIPTION OF THE PRIOR ART

To detect the formation of the bacterial metabolites mentioned above, it has been necessary up to now to pierce the packaging material and to test the gas space above the sample with the use of appropriate sensors for oxygen, $CO_2$ and other gases. Suitable sensors would be amperometric oxygen sensors or potentiometric $CO_2$ sensors.

The disadvantage of such methods is that they necessitate the use of suitable sampling and evaluation equipment, and that tile packaging material must be pierced, such that the particular food will no longer be sterile after testing. Besides, manipulation requires a certain skill as careless opening of the packet may impair the measured results due to a rapid gas exchange.

Similarly, packaged pharmaceuticals, drugs and cosmetics release certain gases upon bacterial or non-bacterial, e.g. hydrolytic decomposition, or they consume a gas, such as oxygen or carbon dioxide. Such decomposition processes can hardly be recognized from outside, as the amounts of the substances formed or consumed often are very small indeed.

In this context, a color indicator is known from U.S. Pat. No. 4,746,616, which may be added to food, drugs or dietary products, and which responds to toxic contaminants or agents entering the package due to careless handling or intentional contamination, by a detectable change in color. The non-toxic color indicator may be placed inside the cap of a phial, for instance, and will exhibit a change in color upon contact with cyanides, for example. With this method it is not possible, however, to detect the decay of organic substances, or their decomposition due to the activity of bacteria, since no additives or contaminants are involved in this case.

In U.S. Pat. No. 3,198,163 a moisture indicator is described, which is placed on the inside of a packaging material for use with products whose quality might be impaired by too much moisture. If a certain moisture level is surpassed, the indicator will respond by a change in color, which can be noted or detected from outside.

A similar effect is obtained with the thaw sensor disclosed in U.S. Pat. No. 2,762,711, which can be used to find out whether frozen food has been subject to short-term thawing before being frozen once more. For this purpose an indicator responding to the contact with liquid water by a color change is placed inside the box or wrapping containing the frozen product in such a way that it may be reached by thaw water. Upon contact with water this indicator will show an irreversible change in color. It cannot be used to detect any beginning or progressive decay of packaged organic products, however.

SUMMARY OF THE INVENTION

It is an object of the invention to provide a method which is easy to apply and does not require opening of the package. Another concern of the invention is to propose a good packaging material for use with this method.

In the invention this object is achieved by sealing the organic substance together with an optical sensor element so as to be gas-tight, thus bringing it into contact with the gas phase between organic product and packaging material, —such that any change in the composition of the gas phase due to a decay of the organic substance will lead to a change in an optical property, preferably a change in the color or fluorescence of the sensor element —, and by detecting the change in this optical property by visual or opto-electronic means.

In this context either an increase in the $CO_2$-, $H_2S$-, mercaptan-, ammonia- or amine-content, a decrease of the $O_2$ content of the gas phase, or a decrease of $O_2$ content and an increase of at least one value of $CO_2$, $H_2S$, mercaptan, ammonia or amine content of the gas phase is measured.

The method of the invention thus is based on the use of optical sensors, which are applied on the inside of the packet and therefore are in permanent contact with the gas phase above the sample, or with the sample itself. These sensors are configured as planar elements responding to the formation of $CO_2$ or odorous substances from the sulfide or amine group by a visually or instrumentally detectable change in their natural color or fluorescence. Similarly, the inside of the packaging may be provided with sensor elements indicating the consumption of oxygen.

For a packaging material for use with the method, which carries a planar optical sensor element on its inside facing an organic substance to be packaged, —this packaging material being transparent to the radiation to be detected by visual or opto-electronic means at least in the area of the sensor element —, the invention provides that the sensor element be placed in the gas phase above the organic substance, and that it be provided with an indicator substance responding to a change in the gas composition inside the package by a change in its optical properties. In this way the change in color may be determined purely visually, i.e., without any evaluation device, in the simplest case of the invention.

The packaging material including the optical sensor may be provided with an optical evaluation unit, which may be brought into contact with the sensor element by moans of optical waveguides, preferably fiber optics, the evaluation unit being provided with a device indicating a change in the color or fluorescence of the sensor element. If the sensor element contains a fluorescence indicator, the optical evaluation unit will provide the necessary excitation radiation.

In order to prevent non-gaseous substances present in fresh food from effecting a change of color or fluorescence of the sensor surface, a further development of the invention proposes that the indicator substance be provided in an indicator layer, whose side facing the organic product is covered by a gas-permeable, hydrophobic polymer film, or rather, that the sensor element be made of a gas-permeable, hydrophobic polymer film containing the indicator substance as droplets of an aqueous or organic-aqueous emulsion. The necessary selectivity for the gaseous substances or vapors to be detected preferably is obtained with the use of organic polymers, such as silicones.

In the invention an adhesive layer is provided between the packaging material and the planar sensor element, the inner surface of the packaging material facing the sensor element being etched or chemically modified in this area, if necessary, in order to improve the adhesion of the sensor element.

To make color changes in the sensor element or the indicator layer more apparent, preferably white pigments may be incorporated into the indicator layer or polymer film. In this way color changes are easily detectable despite the natural color of a sample (e.g. a meat sample).

Finally, the invention provides that the packaging material have reference areas of a given color in the regions adjacent to the sensor element, which reference areas, if visually compared with the sensor element, will give information on the freshness of the organic product packaged. For instance, reference strips consisting of an indicator-free, pigmented polymer film may be used, which will strongly contrast with the indicator layer if the latter changes its color.

BRIEF DESCRIPTION OF THE DRAWINGS

The invention will now be further described by way of example only with reference to the accompanying drawings, in which.

DETAILED DESCRIPTION OF THE PREFERRED EMBODIMENT

Figure 1:
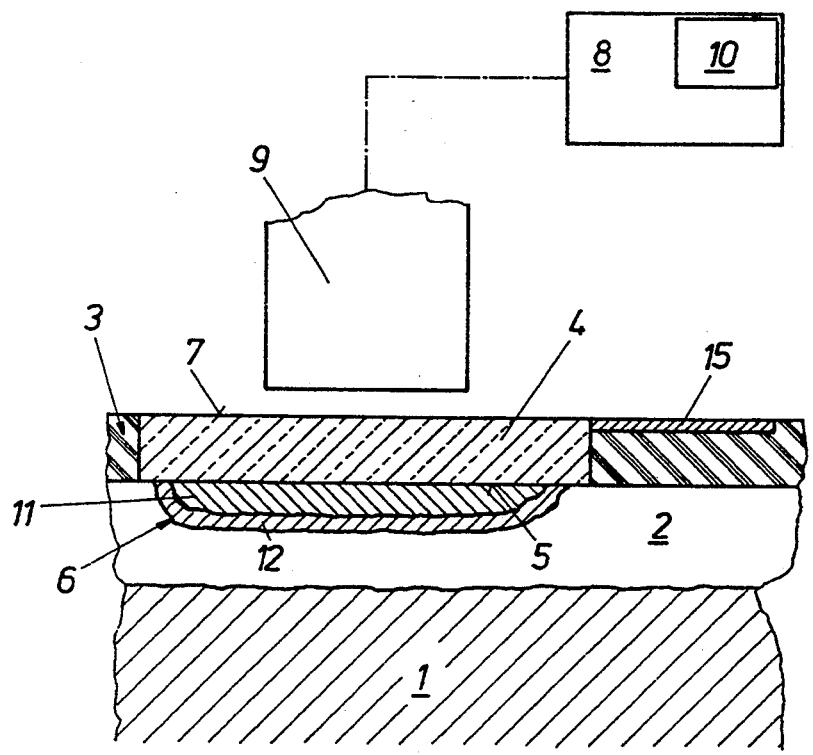
FIG. 1 shows a device with a packaging material as proposed by the invention, and FIG. 2 a variant of FIG. 1.
Figure 2:
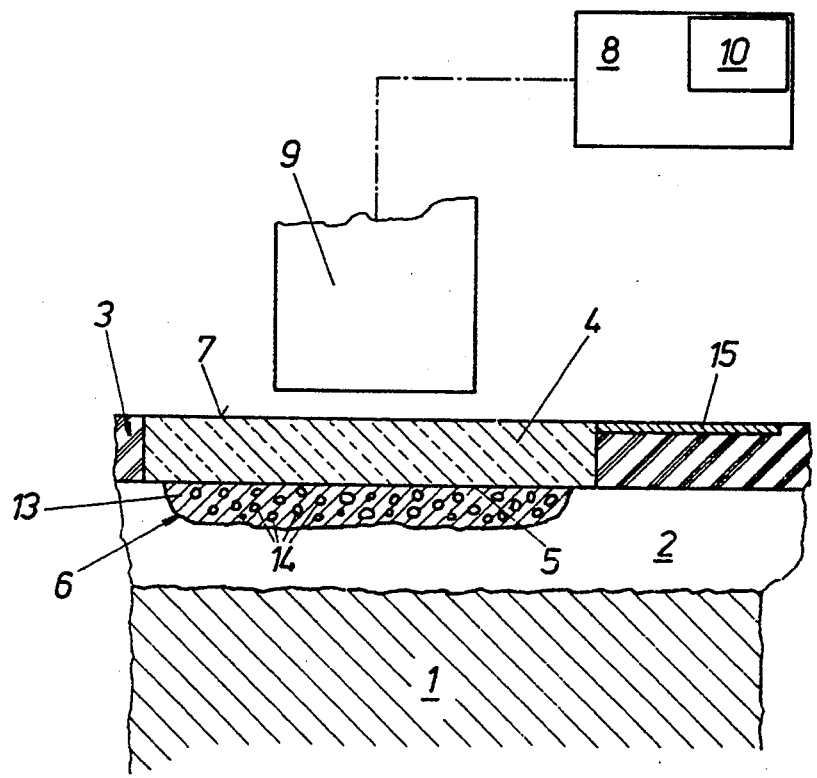

In both FIGS. 1 and 2 the organic substance, or rather, the food product to be packaged, has the reference number 1, the gas space above is 2 and the packaging material 3. On the inner surface 5 of the packaging material 3, in an area 4 transparent to the radiation to be measured, a planar optical sensor element 6 is situated, which may be partially in contact with the food product I and may have different structures. On the side 7 facing away from the sensor element 6 either visual monitoring of the color change takes place or an optical evaluation unit 8 is provided, which is in optical contact with the sensor element 6, for instance, via a fiber-optical lightguide 9. The evaluation unit 8 is provided with a device 10 indicating the change in color or fluorescence. If a fluorescence indicator is used in the sensor element 6, the excitation radiation required may be supplied via a two-arm lightguide.

The device, or rather, the packaging material of FIG. 1, has a sensor element 6 whose indicator layer 11 is covered by a gas-permeable, hydrophobic polymer film 12. The gas forming in the organic substance 1 as a result of bacterial decomposition passes through the polymer film 12 before reaching the indicator layer 11, where it effects a change in color or fluorescence.

In the device of FIG. 2 the sensor element 6 consists of a gas-permeable, hydrophobic polymer film 13 containing the indicator substance as droplets of an emulsion 14. The reaction phase itself is an emulsion of a solution of chromogenic or fluorogenic dyes, or dyes whose fluorescence is quenchable, in a solvent which is immiscible with the polymeric material of the polymer film 13. The formation or consumption of gaseous substances will cause n change in color or fluorescence, which is detected either purely visually, or with the use of the fiber optic 9 and an appropriate evaluation unit 8.

Typical film thicknesses of the sensor elements shown in FIG. 1 and 2 are 20–500 micrometers.

The packaging material 3 may further be provided with colored areas in the regions 15 adjacent to the sensor element 6. The extent to which the colors of such an area and the sensor element 6 match or contrast will permit to determine whether a product is fresh or tainted.

EXAMPLES (1) Packaging material with an emulsion layer for optical detection of the formation of hydrogen sulphide.

20 grams SiliconBasis PE 1055A (Petrarch Systems Silanes & Silicones, ABCR GmbH, D-7500 Karlsruhe, Germany; all other silicones are also obtained from this company) and 6 microliters polymerization inhibitor PS 925 are mixed and cooled to approximately 0° C. To this is added in small portions 4 grams of a 40% solution of lead(II) nitrate in water, which additionally contains 34 milligrams sodium lauryl sulphate and in which 2% titanium dioxide has been emulsified. With the use of a high- speed stirrer (Virtis type 23, The Virtis Co., Gatdiner, N.Y. 12525) a coarse emulsion is prepared by stirring at speed level 10–15 for 15 seconds. After all ingredients have been added they are processed into a fine emulsion by stirring at level 30–40.

The emulsion obtained in this manner is mixed with a curing component for cross-linking. For this purpose 2 grams of the silicone curing agent PE 1055B are added to the above fine emulsion at room temperature, using a Pasteur pipette. The material is then coated onto the packaging material to the desired extent and thickness, and is left to cure either for 24 hours at room temperature or for 2 hours at 50° C. A white sensor surface is obtained, which will turn to a greyish brown and then to black upon contact with hydrogen sulphide (H2S). The change in color is made visible even better by placing a second membrane next to the sensor membrane, which may be produced by preparing a suspension of titanium oxide in the above silicones. Due to tile absence of the lead nitrate emulsion colors will remain unaltered in this instance, which will greatly facilitate detection of even minute color differences. Instead of lead nitrate, other heavy metal salts may be used in aqueous solutions (e.g., mercury or cadmium salts).

(2) Packaging material with a membrane for optical detection of the formation of ammonia and amines.

By reacting tile 40% solution of lead(II) nitrate in water with a solution of 5 milligrams Carboxy-SNARF-X (5′ and 6′)-carboxy-3-hydroxy-tetrahydroquinolizino

[1,9-hi] spiro [7H-benzo[c]xanthene-7,1'(3'H)-isobenzofuran]-3'-one) of Molecular Probes Inc., Eugene, Oreg., SNARF being a trademark of this company, in 10 milliliters bicarbonate buffer of pH 7.0, a membrane emulsion is obtained with the procedure of Example (1), whose color will change from purple to blue by exposing it to gaseous ammonia or evaporable amines. Dyes from the group of naphthorhodamines or naphtho- fluoresceins (e.g., carboxy-naphthofluoresceins) may also be used.

(3) Packaging material with a membrane for optical detection of the formation of $CO_2$.

Fine particles of polyacrylic amide (particle size 2–50 micrometers) are added to a concentrated solution of bromothymol blue in a 1:1 mixture of bicarbonate phosphate buffer (pH 8.2 to 8.5) and methanol. After 6 hours the particles are removed, dried and applied in a thin layer on the packaging material over a thin coat of a primer (e.g., an adhesive coating, product #46.960 of Whittaker Chemicals, Brussels, Belgium). At 85° C. the particles are anchored in this coating within 5 minutes. Then the specimen is allowed to rest at room temperature. Tile particles are gently pressed and covered by a thin (12 micrometers) membrane of a $CO_2$-permeable polymer (e.g., silicone-carbonate copolymer, polyurethane or silicone). The edge of the cover membrane should extend beyond the blue edge of the sensor surface in order to ensure proper sealing of the edges. After immersing the specimen in water for 24 hours a planar sensor element is obtained (cf. FIG. 1), which will change its color from blue to green to yellow when it is treated with $CO_2$. For the detection of ammonia it will also be possible to immobilize Carboxy-SNARF-X on the polyacrylic amide particles by covalent bonding instead of using bromothymol blue.

Similarly, a great number of test reactions based on color changes—as described in the respective literature for a variety of gases—may be used for quality control, either by using watery emulsions of the appropriate reagents as membrane materials (FIG. 1), or by immobilizing the reagents on a solid substrate, covering them with a gas-permeable polymer film as described in Example 3 and applying them on an area of the packaging material (FIG. 2). With respect to the embodiment of the invention wherein both a decrease in $O_2$ content and an increase in at least of one value of $CO_2$, $H_2S$, mercaptan, ammonia or amine content of the gas phase due to organic substance decay are detected, suitable indicators are disclosed in U.S. Pat. No. 5,108,932, the contents of which is incorporated by reference. Alternatively, two indicator substances can be used, e.g., one for detecting $O_2$ content and one for detecting $CO_2$ content, as disclosed in U.S. Pat. No. 5,114,676, the contents of which is also incorporated by reference. A measuring device for determining $O_2$ content is, e.g., disclosed in European Patent No. 105,870.

We claim:

1. A packaging material having an inside surface which can face a gas phase above an organic substance to be packaged, wherein said packaging material comprises at least one transparent portion which is transparent to radiation to be detected by visual or opto-electronic means, and further comprises a planar optical sensor element fastened to an inside surface at said transparent area and of being in contact with a gas phase above an organic substance, and wherein said planar optical sensor element is provided with an indicator substance responding to a decrease of $O_2$-content and an increase of at least one value of $H_2S$-, mercaptan-, or amine-content in said gas phase with a change of fluorescence.

2. A packaging material according to claim 1, wherein said indicator substance is provided in an indicator layer, having a side facing said organic substance, which is covered by a gas-permeable, hydrophobic polymer film.

3. A packaging material according to claim 2, wherein said indicator layer consists of polyacrylic amide particles in which said indicator substance is provided in a buffer solution.

4. A packaging material according to claim 3, wherein said indicator substance is bromothymol blue for the detection of $CO_2$.

5. A packaging material according to claim 2, wherein said indicator layer consists of polyacrylic amide particles on which the indicator substance is immobilized.

6. A packaging material according to claim 5, wherein said indicator substances is (5'(and 6')-carboxy-3-hydroxy-tetrahydroquinolizino[1,9-hi]spiro[7H-benzo[c]xanthene-7,1'(3'H)-isobenzofuran]-3'-one) for the detection of ammonia.

7. A packaging material according to claim 2, wherein white pigments are added to said indicator layer or said gas-permeable, hydrophobic polymer film.

8. A packaging material according to claim 1, wherein said planar optical sensor element is made of a gas-permeable, hydrophobic polymer film containing said indicator substance as droplets of an aqueous or organic-aqueous emulsion.

9. A packaging material according to claim 8, wherein said indicator substance used for detecting $H_2S$ contains an aqueous solution of a heavy metal salt.

10. A packaging material according to claim 9, wherein said heaving metal salt is lead(II) nitrate.

11. A packaging material according to claim 8, wherein said indicator substance used for detecting ammonia and amines contains -(5'(and 6')-carboxy-3-hydroxy-tetrahydroquinolizino[1,9-hi]spiro[7H-benzo[c]xanthene-7,1'(3'H)-isobenzofuran]-3'-one)- or carboxy-naphthofluoresceins.

12. A packaging material according to claim 1, wherein said inside of said packaging material facing said sensor element is etched or chemically modified and an adhesive layer is provided between said packaging material and said planar optical sensor element.

13. A packaging material according to claim 1, further including reference areas of a given color in regions adjacent to said planar optical sensor element for visually comparing said reference areas with said sensor element, thus providing information on freshness of said organic substance packaged.

14. Method for the quality control of packaged organic substances, from the group of foods, luxury foods and drugs, comprising the steps of:
  a) sealing an organic substance together with an optical sensor element in a gas-tight manner within a packaging material;
  b) bringing said optical sensor element into contact with a gas phase between said organic substance and said packaging material, wherein a decrease of $O_2$-content and an increase of at least one value of $H_2S$-, mercaptan- or amine-content of said gas phase due to a decay of said organic substance leads to a change of fluorescence of said optical sensor element; and c) detecting said change of fluorescence by visual or optoelectronic means.

15. Method for the quality control of packaged organic substances, from the group of foods, luxury foods and drugs, comprising the steps of:
  a) sealing an organic substance together with an optical sensor element in a gas-tight manner within a packaging material;
  b) bringing said optical sensor element into contact with a gas phase between said organic substance and said packaging material, wherein a decrease of $O_2$-content and an increase of at least one value of $CO_2$-, $H_2S$-, mercaptan-, ammonia- or amine-content of said gas phase due to a decay of said organic substance leads to a change of fluorescence of said optical sensor element; and
  c) detecting said change of fluorescence by visual or optoelectronic means.

* * * * *